United States Patent [19]

Ito

[11] Patent Number: 5,024,758

[45] Date of Patent: Jun. 18, 1991

[54] HORIZONTAL FLOW-THROUGH COIL PLANET CENTRIFUGE WITH MULTILAYER PLURAL COILS IN ECCENTRIC SYNCHRONOUS ROTATION, SUITABLE FOR COUNTER-CURRENT CHROMATOGRAPHY

[75] Inventor: Yoichiro Ito, Bethesda, Md.

[73] Assignee: The United States of America as represented by the Department of Health and Human Services, Washington, D.C.

[21] Appl. No.: 496,144

[22] Filed: Mar. 19, 1990

Related U.S. Application Data

[63] Continuation of Ser. No. 287,664, Dec. 20, 1988, abandoned.

[51] Int. Cl.⁵ .............................................. B01D 15/08
[52] U.S. Cl. .................................. 210/198.2; 210/657
[58] Field of Search .................... 210/657, 198.2, 198.3

[56] References Cited

U.S. PATENT DOCUMENTS

| | | | |
|---|---|---|---|
| 3,775,309 | 11/1973 | Ito | 210/657 |
| 4,058,460 | 11/1977 | Ito | 210/198.2 |
| 4,066,553 | 1/1978 | Bardonnet | 210/490 |
| 4,211,658 | 7/1980 | McDonald | 210/198.2 |
| 4,250,035 | 2/1981 | McDonald | 210/198.2 |
| 4,321,138 | 3/1982 | Ito | 210/657 |
| 4,324,661 | 4/1982 | Ito | 210/657 |
| 4,484,061 | 11/1984 | Zelinka | 210/198.2 |
| 4,487,693 | 11/1984 | Ito | 210/657 |
| 4,554,436 | 11/1985 | Chlosta | 210/657 |
| 4,615,805 | 10/1986 | Ito | 210/657 |
| 4,657,742 | 4/1987 | Beaver | 210/509 |

OTHER PUBLICATIONS

Ito, Efficient Preparative Counter-Current Chromatography with a Coil Planet Centrifuge, Journal of Chromatography, 214 (1981), pp. 122-125.

Primary Examiner—Ernest G. Therkorn
Attorney, Agent, or Firm—Lowe, Price, LeBlanc, Becker & Shur

[57] ABSTRACT

A horizontal flow-through coil centrifuge provides a very long continuous partition facilitating passage through a plurality of serially connected multilayer helical tubing coils subjected to a rotary motion at a selected angular velocity about a column assembly axis and, simultaneously, a revolving motion of that axis about a stationary horizontal axis at the same angular velocity therearound. The passage of a fluid mobile phase containing solute through the very long length of tubing generates a commensurately long dwell time of the solutes in the complex gravitational/centrifugal acceleration field through a relatively large volume of a fluid stationary phase held in the moving tubing, thus enabling very sensitive chromatographic separations of constituents between the two fluid phases. Gearing and speed and temperature controls are provided in the apparatus to ensure that inflow/outflow tubing remains free of twisting and allowing use at a variety of operational speeds and fluid temperatures.

17 Claims, 2 Drawing Sheets

HORIZONTAL FLOW-THROUGH COIL PLANET CENTRIFUGE WITH MULTILAYER PLURAL COILS IN ECCENTRIC SYNCHRONOUS ROTATION, SUITABLE FOR COUNTER-CURRENT CHROMATOGRAPHY

This application is a continuation of application Ser. No. 287,664, filed Dec. 20, 1988, now abandoned.

FIELD OF THE INVENTION

This invention relates to continuous countercurrent chromatography systems and, more particularly, to a centrifuge system for high volume continuous countercurrent chromatography that employs a plurality of serially connected multilayer tubular coils in synchronous eccentric rotation about a horizontal axis.

BACKGROUND OF THE RELEVANT ART

During the past decade, a variety of horizontal flow-through, coil planet centrifuges have become available that are particularly suitable for performing preparative countercurrent chromatography (CCC, hereinafter). Examples of such devices include my U.S. Pat. Nos. 4,058,460 disclosing a horizontal flow-through, coil planet centrifuge without rotating seals, in which the planetary motion allows both gravitational and centrifugal force fields to act in a time-varying manner to provide highly efficient mixing of two solvent phases in the coil for chromatographic separations of constituents therebetween; No. 4,324,661 claiming methods for centrifugal CCC extraction of separable components from a liquid sample comprising two respective solvent phases of different viscosity and density through opposite ends of an axially rotating column wherein a liquid sample is introduced at a middle portion of the column and a selected separable component of the sample is collected from one of the two ends of the column; and No. 4,487,693 disclosing a multilayer coil countercurrent chromatograph with adjustable revolutional radius to enable an adjustment of the so-called "$\beta$" value of the device to make it substantially greater than 1. $\beta$ may be defined in terms of the geometry of such systems as the ratio of the radius characterizing rotation of the tubing coil about an axis of a holder to the radius at which the axis of this holder revolves around a principal/stationary axis of the system to generate the compound synchronous motion to which fluid flowing through the coil is subjected during use.

Experience with such devices, in which the tubular coil through which the fluid materials are flowed undergoes a synchronous planetary motion about a stationary axis to provide efficient mixing of the two solvent phases, teaches that having the system rotate and revolve about horizontal axes is particularly helpful. Because such a system permits stable retention of low interfacial tension two-phase solvent systems, such apparatus has been extensively used for separations of peptides and other polar compounds with hydrophilic butanol solvent systems. This is described in considerable detail in, for example, Versatile Coil Planet Centrifuge for Performing Countercurrent Chromatography: Comparative Studies on Performance on Three Types of Columns, Sandlin, J.S. and Ito, Y., *Journal of Liquid Chromatography*, 11(1), 55-77 (1988). This article teaches three different column configurations, i.e., coaxial multilayer coil, toroidal coil form, and eccentric dual layer coils mounted around the holder. Among these the concentric multilayer coil arrangement, although it can hold the maximum volume of the solvent, fails to retain the polymer phase systems. The eccentric coil arrangement which relates to the present invention, on the other hand, provides stable retention for all the solvent systems including viscous polymer phase systems.

As is amply disclosed in the references listed hereinabove, and as is well understood by persons skilled in the relevant art, rotation of a helically wound tubular coil about an axis of rotation revolving around a stationary axis creates certain highly desirable effects on fluids inside the coil that are advantageously exploited for chromatographic studies. Revolution of the coil contributes to stabilizing one of the two phases being flowed therethrough, i.e., that phase which may be identified as the "stationary phase", while rotation of the coil about the holder axis produces mixing with the other or "mobile phase" to promote partition processing of solutes therefrom. In order to achieve the best results, these two effects should be optimized to yield a satisfactory retention level of the stationary phase and at the same time generate an efficient mixing of the two phases in the coil. In practice, after the apparatus has been operated for some time, a hydrodynamic equilibrium is obtained in which the stationary phase is retained in the coil and the mobile phase is introduced at an inlet of the coiled tubing elutes through the coil. Samples of materials introduced in solution in the mobile phase are partitioned between the two phases and are separated chromatographically according to their partition coefficients.

As will be immediately apparent, the formation of such a hydrodynamic equilibrium is dependent upon a first set of variables inherent to the solvent system used, e.g., interfacial tension, tube wall affinity, density differences, and the viscosities of the materials constituting the two phases, as well as on a second set of variables related to the physical aspects of the apparatus, e.g., the rotational speed at which the apparatus is operated, the internal diameter of the tubing used, the flow rate of the mobile phase, the relative directions in which the rotation and revolution of the coiled tubing are effected, and the $\beta$ value of the apparatus.

Experimental studies have shown, however, that the formation of this equilibrium is secondary to the acceleration field to which the coiled tubing is subjected. Structures to avoid sealing problems that would otherwise be encountered due to twisting of tubing enabling fluid flow to the rotating coils are described generally in the cited references, especially in my U.S. Pat. No. 4,058,460, which is incorporated herein by reference for its disclosure of a planetary gear system for avoiding flow tube twisting. In summary, a typical structure of this type causes a column holding one or more helical coils of tubing to revolve once with respect to a stationary, central, preferably horizontal axis of the apparatus while simultaneously rotating with the same angular velocity about the rotational axis that is revolving around the stationary axis.

Such an arrangement obviates sealing problems, twisting of the tubing and the like, and generates an acceleration field that varies with the value of $\beta$, the radial span of the tubing coil, and the speed of rotation. Although the centrifugal force field is always directed radially outward, what is radially outward for each point in the coil subjected to synchronous planetary motion varies with time and its instantaneous location and, furthermore, is coupled with the ever present gravitational field acting towards the center of the earth. In effect, therefore, the net acceleration experienced by fluid at any point in the coil subjected to synchronous planetary motion as indicated is constantly varying in time.

The acceleration field also generates centrifugal forces on the columns or formers about which the liquid filled tubing is coiled. While higher partition efficiencies may be obtained by providing longer lengths of tubing coil, the very length of such an element will lead inevitably to potentially unacceptable physical deformation due to centrifugal forces acting thereon during use. One solution clearly is to shorten the overall length of the helical coil, and one way to counter a corresponding diminution of the overall length of tubing and the net volume of liquid subjected to the acceleration field within the coil is to form a multilayer coil. My, U.S. Pat. No. 4,487,693 discloses the use of a single multilayer coil in an apparatus in which a physical central shaft is eliminated to obtain values of $\beta$ greater than 1. However, the need for longer tubing length and liquid volume within the acceleration field, while limiting centrifugal deformation of the tubing coil itself, remains a factor that calls for further enhancement.

A need, therefore, exists for a device of the type generally described hitherto that permits seal-free provision of inflows and outflows of selected fluids to subject them to strong gravitational-centrifugal acceleration fields in synchronous planetary motion, with limited physical deformation of the apparatus, while providing an extensive length of tubing to conduct mixing fluid flow and of a significant volume of liquid subjected to a strong time-varying acceleration field.

SUMMARY OF THE INVENTION

Accordingly, it is a principal objective of the present invention to provide a centrifuge apparatus suitable for forming countercurrent chromatography that provides a high volume, high residence time for two interacting liquid phases subjected to a combined gravitational-centrifugal acceleration field.

It is another object of this invention to provide apparatus having a high partition efficiency for countercurrent chromatography that is free of sealing problems related to inflows and outflows of partition fluids as these are conducted to and away from strong acceleration fields generated by synchronous planetary motion of substantial lengths of fluid tubing about a stationary horizontal axis.

These and other related objectives are met by providing apparatus suitable for countercurrent chromatography of predetermined fluid flow therethrough, that includes a support, frame means rotatably mounted to said support for rotation about a first stationary axis, column assembly support means, having opposite end portions disposed on a second axis parallel to and separated from said first axis by a first radius $R_1$, rotatably mounted to said frame means for enabling rotation of a column assembly about said second axis while said frame simultaneously rotates about said first axis, a plurality of similar multilayer helical tubing coils each having respective tail and head ends selectively connected to enable continuous fluid flow therethrough, each of said coils being wound about one of an equal number of cylindrical columns of said column assembly each disposed with a corresponding third axis thereof parallel to the first and second axes and symmetrically disposed therearound at a common second radius $R_2$, and means for simultaneously rotating the frame means about the first axis and the column assembly support means about the second axis.

DESCRIPTION OF THE PREFERRED EMBODIMENT

Figure 1:
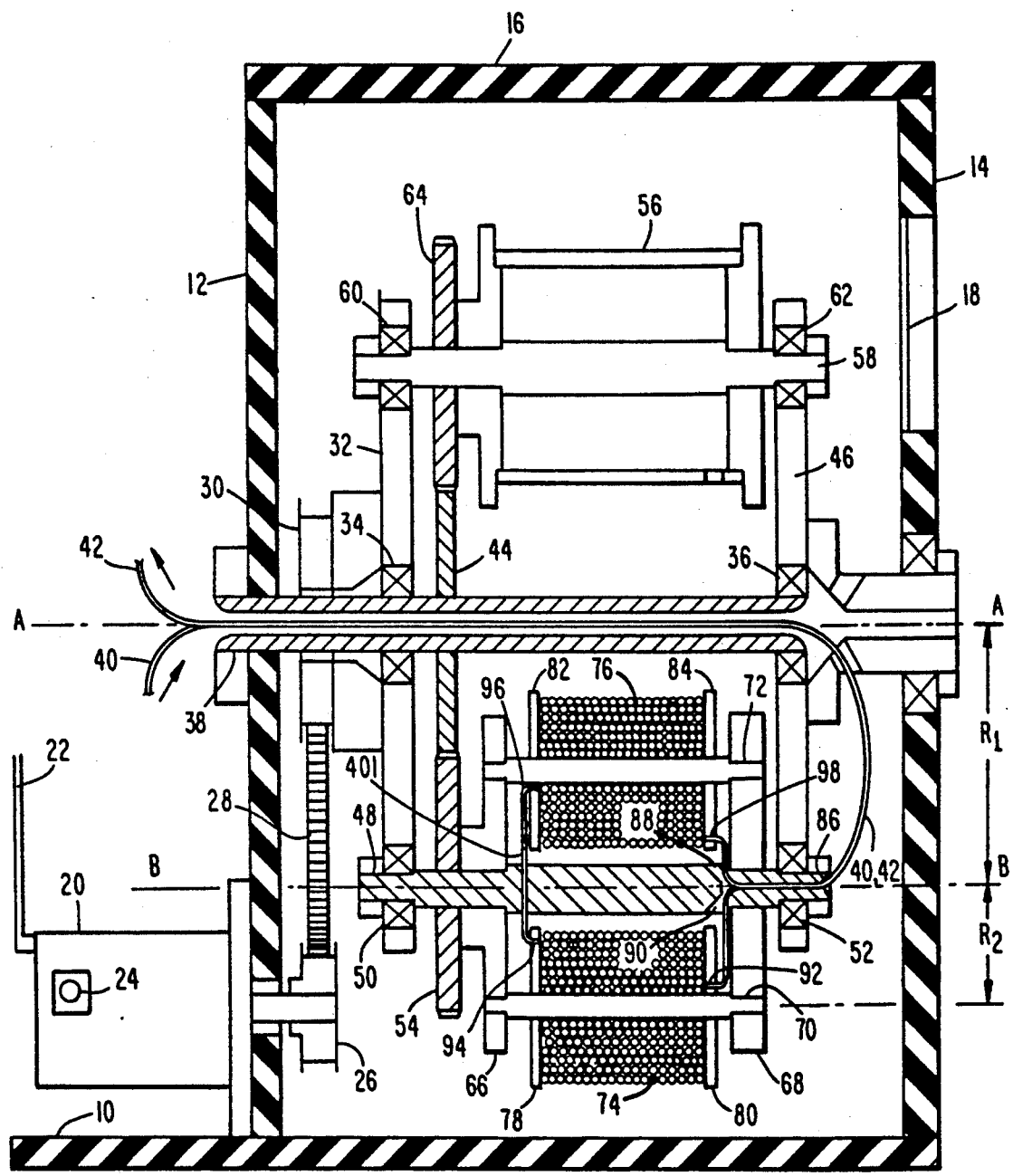
FIG. 1 illustrates in partial vertical cross-section a preferred embodiment of this invention with a single column assembly that has two multilayer interconnected tubing coils and a single counterbalance mass.

As best seen with reference to FIG. 1, the apparatus is formed to have a base 10, exemplary vertical walls 12 and 14 and a top 16, all conveniently incorporating thermal insulation to form a containment chamber within which the rapidly rotating parts are safely and conveniently contained.

The provision of thermally insulating walls to the chamber facilitates temperature control of the environment within which the reacting fluids are flowed through the coils while being subjected to the imposed acceleration field. Small heating pads or the like (not shown) may be provided to add heat to the environment within the chamber as needed. Also, a thermometer or a thermocouple (not shown) may be provided to determine the prevailing temperature inside the chamber while the apparatus is in operation. Such information on the temperature may be utilized with any conventional temperature control device to regulate the amount of heat (or, naturally, cooling if required) needed to suit particular experimental needs.

A transparent window 18 may be provided to enable a user to view the operating elements during use.

An electric motor 20, provided with electrical power through lines 22 from a mains power supply and a known type of speed control 24, is located conveniently at a chamber wall as indicated. A distal end of the motor shaft has a drive pulley 26 which, for example by a toothed belt 28, conveys rotational torque to a driven pulley 30. Pulley 30 and a rotatable frame, formed of two halves 32 and 46 attached thereto, are rotatably supported on bearings 34 and 36 supported on a common stationary horizontal axis A—A by the side walls of the chamber.

A portion of the stationary support attached to the chamber wall consists of a stationary horizontal open-ended tubular member 38, coaxial with axis A—A, that serves as a protective guide to inflow and outflow tubes 40 and 42, through which selected fluid flows may be directed into and out of the coils of the apparatus during use. Although only a single inflow tube 40 and a single outflow tube 42 are illustrated, this is for purposes of simplicity only. By appropriate selection of the sizes of tubular element 38 and fluid tubing employed, a number of such tubes may be protectively guided through tubular element 38 from the outside of the chamber to communicate with selected portions of the rotating elements of the apparatus as more fully described hereinbelow. A portion of tubular member 38, within the chamber, is attached to a stationary gear 44. The two end portions 32 and 46 of the rotatable frame are connected to each other at one side by a column holder shaft 48 supported in bearings 50 and 52 at opposite ends thereof on a horizontal movable axis B—B as illustrated in FIG. 1. Thus, all elements supported by rotatably supported shaft 48 are free to rotate with respect to the frame end portions 32 and 46. The radius at which column support shaft 48 may revolve around the stationary axis A—A of cylindrical element 38 is $R_1$. Column support shaft 48 is attached to a gear 54 having the same effective diameter and number of teeth as stationary gear 44. Upon rotation of the frame 32, 46 about stationary axis A—A by drive pulley 26 coupled to pulley 30, gear 54 will turn about its own axis B—B at the same angular velocity as the frame, i.e., at the same angular speed in rpm and in the same sense or direction of rotation.

In the apparatus per FIG. 1, a counterbalance structure having a mass 56 is provided on a shaft 58 disposed diametrically opposite the axis B—B of column support shaft 48. Shaft 58 is rotatably supported in bearings 60 and 62 and is also connected to a gear 64 similar in shape and number of teeth to stationary gear 44 and rotatable gear 54. Strictly speaking, this counterbalance structure need not be rotatably supported in frame 32, 46 so long as its mass and center of mass are correctly located to provide dynamic balance in known manner. Whether the counterbalance is rotatably supported or not, with a suitable selection of the mass 56, taking into account the mass of the rotatable elements supported and rotating with shaft 48, very precise rotational dynamic balancing of the entire rotatable assembly may be readily obtained.

For ease of reference, stationary gear 44 will be referred to as the "sun" gear and rotatable gears 54 and 64 will be referred to as the "planet" gears. When frame 32, 46 revolves at a selected angular velocity about stationary axis A—A, due to the engagement of the planet gears 54 and 64 with sun gear 44 both the balance mass 56 and the column support shaft 48 will turn with the same angular velocity with respect to frame elements 32 and 46 but at twice that angular velocity as seen from the point of view of the user stationary in inertial space. My previously cited U.S. Pat. No. 4,058,460 is expressly incorporated herein by reference for its illustration in FIG. 2 of this aspect of the dynamics of such a geared system. A direct and necessary consequence of this arrangement is that no matter how much the rotatable elements are turned, the lengths of tubing 40 and 42 that are led through cylindrical element 38 to column support shaft 48 never become twisted. This obviates all need for complex and generally unsatisfactory rotary seals in the device. My earlier patents have utilized this principle and it is, therefore, well known to those skilled in the art and will not be described further for this reason.

Column support shaft 48, conveniently at gear 54 affixed thereto, supports a column assembly formed of end elements 66 and 68 separated by and affixed to each other by coil support columns 70 and 72 which have wound around central portions thereof multilayer helical coils of tubing 74 and 76, respectively, between flat disk-like end pieces 78 and 80 (for column 70) and 82 and 84 (for column 72). The axes of coil support columns 70 and 72 are at equal radii $R_2$ from axis B—B. Hence $\beta = (R_2/R_1)$.

Inflow and outflow tubings 40 and 42, guided out of stationary central tubular element 38, are passed into an axial hole 86 at a nearby end of shaft 48. They are then led out through radially disposed holes 88 and 90 in shaft 48 as indicated.

Inlet flow tube 40, for example, may be passed through radially disposed hole 90 of shaft 48 and led through an aperture 92 of disk element 80 to be contiguously connected to one end, e.g., the "head" end, of the length of the multilayer tubing coil 74. At the "tail" end of the entire length of this multilayer tubing coil 74, through an aperture 94 in disk 78 a short piece of tubing 401 contiguously connected thereto then conveys the fluid flow through an aperture 96 to continue the flow through the full length of multilayer helically wound coil 76 and, at the far end thereof, through aperture 98 in disk 84 and out as tube 42 exiting central hole 86 of shaft 48. It then returns via central stationary cylindrical element 38 to take the outflow out of the system.

At all points where the relatively fragile tubing makes contact with hard components of the apparatus, e.g., as it is being guided through cylindrical stationary member 38 or hole 92 in disk 80 to multilayer coil 74, additional protection may be provided by applying thereat a small quantity of a grease-like lubricant and/or a tough flexible sheath (not shown) in conventional manner.

The tubing used for fluid inflow/outflow and to form the multilayer coils preferably, is commercially available small-bore 1.6 mm internal diameter polytetrafluoroethylene (PTFE) tubing. The multilayer coils may conveniently be wound onto a column or shaft, e.g., 70, made of a low mass density metal such as aluminum to reduce extraneous centrifugal loads on the bearings and drive motor of the apparatus. Also, to ensure the geometric integrity of each multilayer coil a conventional, lightweight, heat-shrinkable film layer (not shown) is conveniently applied outside of the outermost layer of tubing coil thereon. This will help to significantly reduce the danger of the fluid-filled outermost layers of coiled tubing from deforming during high-speed operation of the apparatus.

In summary, the principal advantages available from this invention over the known art, including my own inventions cited herein, are the provision of very long zones facilitating interactions between the stationary and mobile fluid phases in the serially connected extensive lengths of tubing formed into a plurality of multilayer coils, without requiring large maximum radii during rotation/revolution motions thereof; the provision of a much larger volume of reactant subjected to the desired acceleration field; and, in relation thereto, long dwell time for each element of the reactants in the acceleration field in passing through the full length of the serially connected coiled tubing. These benefits make the invention highly suitable for analyses/experimentation with reactants that inherently have slower separation rates, require fine measurements of significant parameters, and the like. Thus, chromatographic studies can be extended to studies not hitherto possible.

To ensure acceptable conciseness of this disclosure by avoiding needless repetition of known aspects of principles of operation, structure or rationale for selecting physical parameters and the like, my earlier-cited references are expressly incorporated herein for the following: U.S. Pat. No. 4,058,460 for its illustration per FIG. 2 and related discussion of the manner in which synchronous planetary gearing permits operation of such devices without twisting of inflow/outflow tubing (hence elimination of the need for complex rotary seals); U.S. Pat. No. 4,324,661 for its illustrations per FIGS. 1–5 and related written discussion of synchronous planetary motion, the consequential acceleration field, identification of head and tail ends of a tubing coil and techniques for connecting related lengths of tubing; U.S. Pat. No. 4,487,693 for its discussion, especially at column 1 thereof, of the meaning and practical significance of the β value as it relates to synchronous planet coil-type centrifuge operations; and "Countercurrent Chromatography", pages 55-73 (1988) for its discussion of the principles of countercurrent chromatography and the experimental benefits accruing from use of multilayer coils in the present context.

The basic structure of the apparatus having been described, a brief description is provided hereinafter of a typical experimental study that was conducted with a prototype of the preferred embodiment of this invention.

DESCRIPTION OF THE TYPICAL USE OF THE INVENTION

An aqueous-aqueous two-phase polymer system was prepared by dissolving 150 g of polyethylene glycol 1000 (Sigma Chemical Company, St. Louis, MO) and 150 g of anhydrous dibasic potassium phosphate (J.T. Baker Chemical Company, Phillipsburg, NJ) in 900 ml of distilled water. The solvent mixture was thoroughly equilibrated in a separatory funnel at room temperature and the two phases separated shortly before use. The sample solution was prepared from cytochrome C and lysozyme (both from Sigma Chemical Co.), each 100 mg, by dissolving the mixture in 3 ml of the above solvent system.

The experiment was initiated by filling the entire column, i.e., the coiled tubing, with the stationary/upper phase. This was followed by sample injection through a sample port outside the chamber per FIG. 1 (not shown for simplicity) leading to the inflow tube 40. The apparatus frame 32, 46 was then rotated about stationary axis A—A at 800 rpm while the mobile lower phase was eluted through the column at a flow rate of 0.5 ml/min or 1.0 ml/min. The effluent from the outlet of the column, i.e., the outflow from tube 42, was continuously monitored with an LKB Uvicord S at 275 nm and then fractionated into test tubes at 3 ml/tube with an LKB fraction collector. After two peaks were eluted, the apparatus was stopped and the column contents were collected into a graduated cylinder to measure the volume of the stationary phase retained in the column. An aliquot of each fraction was diluted with distilled water and the absorbance was determined with a Zeiss PM6 spectrophotometer at 280 nm and 500 nm (for cytochrome C) to draw a chromatogram.

Figure 2:
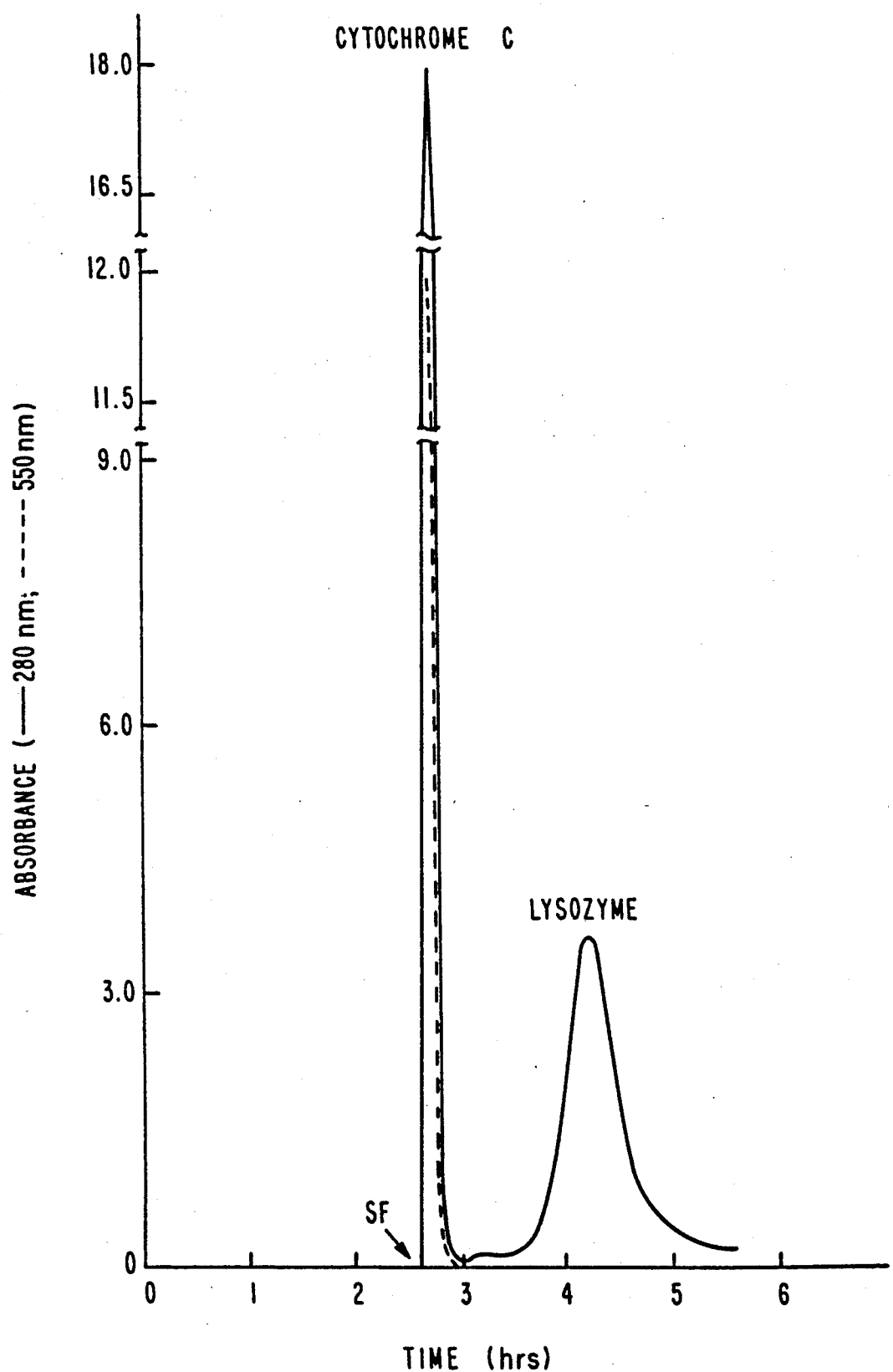
FIG. 2 is a characteristic chromatogram based on an experiment performed with the preferred embodiment of the apparatus.

FIG. 2 shows a chromatogram of cytochrome C and lysozyme obtained with the aqueous-aqueous polymer phase system composed of 12.5% (w/w) polyethylene glycol 1000 and 12.5% (w/w) anhydrous dibasic potassium phosphate in distilled water. The cytochrome C peak was easily identified by its colored fractions measured at 550 nm as indicated by the broken curve. At a flow rate of 1.0 ml/min, the two peaks were completely resolved in 5 hours. The partition efficiency may be calculated from the chromatogram according to the conventional gas chromatographic formula, i.e., $N=(4R/W)^2$, where N denotes the partition efficiency expressed in terms of theoretical plate number (TP); R, the retention time of the peak maximum; and W, the peak width expressed in the same unit as R. Using the above formula, the partition efficiency computed from the second peak was about 350 TP. The retention of the stationary phase was 25% of the total column capacity and the maximum column pressure measured at the outlet of the pump was 170 psi. Application of a lower flow rate of 0.5 ml/min substantially improved the peak resolution but with a longer elution time of 10 hours.

Among various separation methods, the liquid-liquid two-phase partition method with polymer phase systems is particularly suitable for separations of biopolymers and cell particles, because of its gentle separation procedure with nonhostile environment provided by the media used in separation. However, high viscosity and low interfacial tension between the two phases tend to delay the phase settling resulting in long separation times. Although various known centrifuge devices have been utilized to overcome this problem, the high cost of these instruments generally prevents universal use of the method.

The method described hereinabove, utilizing a multilayer, serially connected multicoil apparatus according to the preferred embodiment of this invention yields a high partition efficiency in relatively short separation times (1 TP is produced in less than 30 seconds), while the apparatus is simple in design and relatively inexpensive. The method itself may be applied to various other biopolymers and cell particles by choosing the proper phase composition. The apparatus of this invention will be extremely useful for separation of various biological samples.

The preceding description is set forth to illustrate various embodiments of the invention and are not intended to limit the scope of the apparatus of the present invention. Additional embodiments and advantages will be apparent to one of ordinary skill in the art in view of the appended claims.

What is claimed is:

1. An apparatus suitable for eccentric continuous countercurrent chromatography of predetermined fluid flow therethrough and for providing stable retention of low interfacial tension, viscous two-phase systems therein, comprising:

a support;

frame means rotatably mounted to said support for rotation about a first stationary horizontal axis;

column assembly support means having opposite end portions disposed on a second axis parallel to and separated from said first axis by a first radius $R_1$, rotatably mounted to said frame means for enabling rotation of a column assembly with respect to said frame means about said second axis while said frame simultaneously rotates about said first axis;

a plurality of similar multilayer helical tubing coils each having respective tail and had ends selectively connected to enable continuous fluid flow therethrough, each of said helical coils being wound about one of an equal number of cylindrical columns of said column assembly about corresponding third axes parallel to said first and second axes and symmetrically disposed therearound at a common second radius $R_2$;

said coils sized and dimensioned to reduce physical deformation due to centrifugal forces acting thereon, and for providing stable retention of low interfacial tension, viscous solvent system; and means for simultaneously rotating said frame means about said first axis and said column assembly support means about said second axis, thereby providing eccentric rotation of said column assembly.

2. The apparatus according to claim 1, further comprising:

means for guiding continuous fluid flow into and out of said helical tubing coils while said frame means and said column assembly means simultaneously rotate about the first and second axes respectively.

3. The apparatus according to claim 2, wherein:
said means for guiding fluid flow comprises inflow/outflow tubing communicating with said tubing coils without twisting during use of the apparatus.

4. The apparatus according to claim 3, wherein:
said means for rotating said frame means and said column assembly support means comprises a stationary gear coaxial with said first axis and a similarly formed rotatable gear attached to said column assembly support means, said rotatable gear being directly engaged to said stationary gear whereby the frame assembly and the column assembly support means both rotate at the same velocity in relation to said first and second axes respectively.

5. The apparatus according to claim 4, further comprising:
means for guiding continuous flow into and out of said helical tubing coils while said frame means and said column assembly means simultaneously rotate about the first and second axes respectively.

6. The apparatus according to claim 3, further comprising:
tubing guide passage means provided coaxially with said first axis to protectively hold and guide therein portions of said inflow/outflow tubing for connecting them with said connected plurality of multilayer coils to enable said continuous fluid flow therethrough.

7. The apparatus according to claim 2, wherein:
at least two similarly formed column assembly support means with corresponding multilayer helical tubing coils and cylindrical columns associated therewith are supported at a common radius $R_1$ and all the tubing coils thereof are serially connected to enable said continuous fluid flow therethrough.

8. The apparatus according to claim 2, further comprising:
means for controlling a speed of rotation of said frame means about said first axis.

9. The apparatus according to claim 1, wherein:
said plurality of multilayer tubing coils are each formed of a predetermined number of helical coils in each of a predetermined number of coil layers, and said individual multilayer coils are serially connected whereby said continuous flow traverses the entire length of tubing in all of the connected tubing coils between said inflow/outflow tubes.

10. The apparatus according to claim 1, further comprising:
balance mass means mounted to said frame means and selected and positioned for providing rotational balance to said rotating frame means during rotation thereof.

11. The apparatus according to claim 10, wherein:
said balance mass means comprises at least one other separation column assembly support means with corresponding similar multilayer helical tubing coils and cylindrical columns associated therewith.

12. The apparatus according to claim 1, further comprising:
means for regulating a temperature of said continuous fluid flow through said connected multilayered tubing coils.

13. The apparatus according to claim 1, further comprising:
means for securely retaining the geometrical integrity of each of said multilayered coils when they are subjected to forces incidental to rotation of the frame means during use of the apparatus.

14. The apparatus according to claim 13, wherein:
said retaining means comprises a layer of heat-shrinkable plastics material disposed peripherally of the outermost layer of each multilayer helical tubing coil.

15. The apparatus according to claim 13, further comprising:
means for guiding continuous fluid flow into and out of said helical tubing coils while said frame means and said column assembly means simultaneously rotate about the first and second axes respectively.

16. The apparatus according to claim 15, wherein:
said means for guiding fluid flow comprises inflow/outflow tubing communicating with said tubing coils without twisting during use of the apparatus;
tubing guide passage means provided coaxially with said first axis to protectively hold and guide therein portions of said inflow/outflow tubing to connect them with said connected plurality of multilayer coils to enable said continuous fluid flow therethrough; and
said means for rotating said frame means and said column assembly support means comprises a stationary gear coaxial with said first axis and a similarly formed rotatable gear attached to said column assembly support means, said rotatable gear being directly engaged to said stationary gear whereby the frame assembly support means both rotate at the same velocity in relation to said first and second axes respectively.

17. The apparatus according to claim 1 wherein said second radius $R_2$ is less than said first radius $R_1$, thereby providing a $\beta$ for the apparatus which is less than 1.

* * * * *